United States Patent
Hob Allah et al.

(10) Patent No.: US 7,297,350 B2
(45) Date of Patent: Nov. 20, 2007

(54) EVAPORATE OF ECBALIUM ELATERIUM FRUIT EXTRACT FOR TREATING VIRAL SYMPTOMS

(75) Inventors: Essam M. A. Hob Allah, Cairo (EG); Said I. A. Shalaby, Cairo (EG)

(73) Assignee: Kentara Research LLC, Kitty Hawk, SC (US)

( * ) Notice: Subject to any disclaimer, the term of this patent is extended or adjusted under 35 U.S.C. 154(b) by 291 days.

(21) Appl. No.: 10/637,686

(22) Filed: Aug. 8, 2003

(65) Prior Publication Data

US 2004/0142052 A1 Jul. 22, 2004

Related U.S. Application Data

(60) Provisional application No. 60/402,375, filed on Aug. 9, 2002.

(51) Int. Cl.
*A61K 36/00* (2006.01)
(52) U.S. Cl. .................................. 424/725; 424/777
(58) Field of Classification Search ................ 424/777, 424/758, 404
See application file for complete search history.

(56) References Cited

U.S. PATENT DOCUMENTS

| | | | |
|---|---|---|---|
| 4,822,512 A * | 4/1989 | Auchincloss | |
| 5,089,474 A | 2/1992 | Castro et al. | |
| 5,118,673 A | 6/1992 | Carpenter | |
| 5,763,430 A | 6/1998 | Zasloff | |
| 6,841,174 B2 | 1/2005 | Shalaby et al. | |
| 2004/0142051 A1 | 7/2004 | Hob Allah et al. | |

OTHER PUBLICATIONS

Mylonakis et al. Plasma Viral Load Testing in the Management of HIV Infection; American Family Physician; Feb. 2001 pp. 1-7.*
HIV/Aids Monitoring; Improved Viral Load Test Approved by FDA; Blood Weekly; Atlanta; Sep. 2002 pp. 1-2.*
Animal Models (HBV0; Trimera Disease Model Developed for Hepatitis B; Cancerweekly Plus; Atlanta; Feb. 1999 pp. 1-2.*
Davis, G. Treatment of Chronic Hepatitis C; British Medical Journal; Nov. 2001 pp. 1-3.*
Nicholson et al. INFLUENZA; The Lancet, Nov. 22, 2003, vol. 362, 9397, pp. 1733-1745.*
Peiris et al. Re-Emergence of Fatal Human Influenza a Subtype H5N1 Disease; The Lancet, vol. 363, Feb. 21, 2004, pp. 617-619.*
Wong et al. Avian Influenza Virus Infections in Humans; Chest; Jan. 2006; vol. 129, No. 1, pp. 156-168.*
David M.R. Culbreth et al; A Manual of Materia Medica and Pharmacology, 1927, two pages.
Loutfy Boulos; Medicinal Plants of the World, published & copyrighted 1983.
Harvey Wickes Felter and John Uri Lloyd, *King's American Dispensatory*, 1898 (5 pages).
Robert T. Gunther, *The Greek Herbal at Discorides*, New York Hafner Press, 1934, p. 547.
E. Yesilada, S. Tanaka, E. Sezik and M. Tabata, "Isolation of an anti-inflammatory principle from the fruit juice of Ecballium elaterium", *J. Nat. Prod.*, 1988 May -Jun., 51(3), p. 504.
A, Favel, H. Mattras, M.A. Coletti-Previero, R. Zwilling, E.A. Robinson and B. Castro, "Protease Inhibitors from Ecballium Elaterium Seeds," *Int. J. Peptide Protein Res.*, 33, (1989), pp. 202-208.
J. Remington et al., editors, *The Dispensatory of the United States of America*, Elaterium, (1918).
*The Merck Manual of Therapeutics and Materia Medica*, Seventh Edition, p. 1365, Merck & Co., Inc., Rahway, N.J. (1940).
William A. Haseltine, "Beyond Chicken Soup," *Scientific American*, vol. 285, Issue 5, Nov. 2001, p. 6.

* cited by examiner

*Primary Examiner*—Patricia Leith
(74) *Attorney, Agent, or Firm*—Robert P. Michal; Frishauf, Holtz, Goodman & Chick, P.C.

(57) ABSTRACT

A broad spectrum anti-viral includes a condensate, made by boiling a filtered residue of the Ecbalium Elaterium plant. The condensate, mixed with water, has been successfully used to treat humans for Hepatitis C, Hepatitis B, Influenza, and the Common Cold. The condensate was also subject in vitro assays. These assays showed antiviral activity, with an acceptable level of toxicity.

10 Claims, No Drawings

EVAPORATE OF ECBALIUM ELATERIUM FRUIT EXTRACT FOR TREATING VIRAL SYMPTOMS

CROSS-REFERENCE TO RELATED APPLICATION

This application claims the benefit under 35 USC 119(e) of Provisional application Ser. No. 60/402,375 filed on Aug. 9, 2002.

BACKGROUND OF THE INVENTION

Viruses plague man. Hepatitis, herpes, certain types of leukemia, influenza, and the common cold are all diseases of viral etiology. Of these diseases, influenza and the common cold are sometimes trivialized. The symptoms of influenza are fever, nasal congestion, headache, and a dry or sore throat. Modern medicine treats these diseases with antibiotics, cortisone and antihistamines. These methods generally address only the symptoms of influenza.

Influenza is caused by filterable viruses. There are true influenza viruses (Influenza Myxovirues A, B&C) and Paramyxoviruses (Parainfluenza viruses 1,2,3,4, mumps, measles and respiratory syncytial viruses). Influenza viruses are unrelated antigenically and do not produce cross immunity to one another. There is rapid mutation of strains and substrains of this virus. These viruses are characterized by low antigenicity; so acquired immunity is of short duration. A person may become inflicted more than once. A vaccine for Influenza must be prepared from the same strain prevalent at that time.

Generally influenza is characterized by headache, fever, myalgia, tracheitis and bronchitis. In severe cases, bronchiolitis and bronchopneumonia may occur from secondary bacterial invasion of lungs.

Parainfluenza viruses cause fever, mild respiratory symptoms and pharyngitis, croup, acute tracheitis and bronchitis in children.

Respiratory syncytial viruses cause in adults cough, minor upper respiratory infections, bronchitis, bronchiolitis and bronchopneumonia.

The mode of transmission of influenza is through droplet infection (direct and indirect). The incubation period is 1-3 days. The attack rate is 10-25% in large communities and 40% in closed ones. The clinical picture starts abruptly with headache, shivering, back pain and temperature increasing rapidly from 38.5 degrees C. to 40 degrees C. during the first 24 hours. Headache is frontal, throbbing and its severity is proportional to the degree of fever. Cough brief and specific, not productive of sputum. Substernal burning pain (tracheitis), dryness and soreness of throat & nasal obstruction with no discharge. Myalgia is early especially in adults (severe aches in back and limbs). Patients may complain of pain on moving eyes. Sweating is marked. For diagnosis; physician generally do not need laboratory investigations; but sometimes to be sure we can isolate the virus from nasal discharge or we search for the antibodies in blood (compliment fixation test and Haemagglutination inhibition test). The period of communicability is from the start of fever.

In uncomplicated influenza; the face is flushed with congested nasal & pharyngial mucosa, few rales over chest, fever is <5 days, cough persists for sometime after subsidence of fever, physical & mental fatigue as well as difficulty in concentration during convalescent stage.

In complicated influenza there is bronchitis, bronchiolitis, pneumonia, carditis, pericarditis and neurological complications. Secondary bacterial infection finds its way to the lungs causing more complications.

Common cold; represents 60 types of Rhinoviruses belonging to Picorna group of viruses. The latter is responsible for the most frequent of all human infections (common cold). Most people suffer from 2-4 colds every year, causing loss of millions of man-hours of work. The incubation period is 1-2 days. On the contrary to influenza, the fever is minimal or even absent. Nasal symptoms predominate, there is excess nasal discharge (minor in influenza, due to severe nasal irritation, followed in 1-2 days by coryza for few days, sneezing & nasal obstruction with thin watery nasal discharge, watery eyes, malaise and sensation of dullness, discomfort. During next 2 or 3 days, systemic symptoms subside & nasal discharge becomes mucoid or mucopurulent and tenaceous.

Herpes Zoster is a viral infection usually referred to as VZV. VZV is the same virus that causes Chicken Pox. Herpes Zoster is also called Shingles. The infection is characterized by localized rash and pain. Untreated, the rash typically lasts 2 to 5 weeks. One unfortunate complication is a persistent pain after the rash has healed. Anyone that has had Chicken Pox has significant chance of getting herpes zoster. The mechanism maybe that the virus lays dormant in the body until there is a break down in the body's immune system. This breakdown occurs and the virus reactivates in the form of herpes zoster or shingles.

Herpes simplex (cold Sores) is caused by a virus, herpes simplex 1 (HSV 1). Herpes simplex (cold Sores) is a viral infection, which attacks the skin and nervous system, and usually produces small, irritating, and sometimes painful fluid-filled blisters on or around the mouth and nose. After the initial outbreak, the virus usually lies dormant in the skin or in nerve tissue until something triggers another eruption.

This invention is a method of treating influenza, the common cold, sinusitis, herpes zoster, and herpes simplex by using one single antiviral.

The inventors for many years worked on treatments for hepatitis. Some herbs, combinations of herbs and extracts of herbs were thought to be effective against hepatitis. One inventor, Said Shalaby, is a practicing physician in Cairo, Egypt. In treating many patients with herbal remedies over a nine-year period, Shalaby could not recall a single case of a patient having either a common cold or influenza when the patient was undergoing a herbal treatment. Most of the patients were infected with hepatitis, either Hepatitis C or Hepatitis B. As the purpose of the various herbal treatments was to reduce the viral load, it was concluded by inventor, Said Shalaby, that the herbs contained a general anti-viral, effective against two forms of hepatitis, the subject of a prior US Patent application by the two inventors here and apparently effective against other diverse viruses such as those which cause influenza, the common cold and herpes zoster.

A survey of anti-viral drugs now marketed listed some 24 different drugs. (Scientific American November 2001, page 61) Each drug was designed to combat a particular virus, or to work in combination with another of the listed drugs to combat a particular virus. None are generic anti-virus remedies. Judging from the range of different viruses, which this invention is an effective treatment, it appears that, in addition to being a treatment for the virus mentioned within the examples below, the invention is a generic anti-viral.

DESCRIPTION OF THE INVENTION

The inventors have previously developed a treatment for both Hepatitis C and Hepatitis B, along with other virus caused disease. The prior attempts involved many different herbs. Some were thought to be anti-viral and some had the purpose of reducing or eliminating side effects. Each treatment had at least ten herbs or extracts from herbs. After a study of United States Federal Drug Administration proposed regulations for the control and manufacture of herbal medicines, the inventors sought to develop a treatment in which only one or two herbs or extracts from herbs would be used.

One of the extracts was from the herb, *Ecbalium Elaterium*. This herb had long been used to treat liver disease such as jaundice. (See, "Medicinal Plants of North Africa", Loutfy Boulos, Reference Publications, Inc 1983, page 75) *Ecbalium Elaterium* could not be used directly as it has some serious toxicity problems.

See: A Manual of Materia Medica and Pharmacology by David M. R. Culbreth, Ph.G., M.D. (1927) which described the properties of *Ecbalium Elaterium* as follows:

"PROPERTIES.—Hydragogue cathartic (most powerful known), producing profuse watery evacuations with griping and much prostration; large doses nauseate, vomit, inflame stomach and bowels, increase flow of urine, and may kill. Does not vomit nor purge dogs, rabbits, but kills them by convulsions. Those working in it often have ulcerated fingers, eyes, etc".

Initially the inventors obtained an extract of *Ecbalium elaterium* preparing herbal drops made by using the fruit of *Ecbalium elaterium* and washing the fruit with clean water. Approximately a half-kilogram of fruit and one liter of distilled water were combined in an ordinary house electrical grinder. The fruit was ground for two minutes. The mixture was then poured through a sieve of cotton gauze to separate out the larger fruit particles. The mixture was then filtered using Wattmann filter paper. The filtrate (i.e., cell sap) was stored in a refrigerator at 10° C. for approximately 5-7 hours to promote the precipitation of microparticles. The filtrate was then filtered using ceramic sterilization candles to remove any microorganisms. The pH was adjusted to approximately 6.8-7 using dilute sulfuric acid and sodium bicarbonate. A preservative (thiomersal) was added to the sterilized filtrate to provide a concentration of 0.001 gm/liter. The herbal solution was then placed into 10 cc. dropper bottles under aseptic conditions and stored in the refrigerator at about 4 degrees C. The final concentration of the extract was approximately 0.5 weight % cell sap based on the amount of cell sap dissolved in water (5 gms/1000 ml).

This method did produce a successful anti-viral but those treated with *Ecbalium elaterium* did require additional herbs to minimize side effects. As a result, the treatment had too many herbs, making its future manufacture unfeasible.

The inventors noticed that after placing aluminum foil over the *Ecbalium elaterium* mixture (in order to protect it from dust), a brown residue would form on the foil. They then isolated the residue and reduced it to liquid form so as to be administered in drops.

Once while working with the vapor from the *Ecbalium elaterium*, one of the inventors, Hob Allah, noticed that he was relieved of influenza symptoms within a day rather than the usual 4-6 days he had experienced in the past. To confirm this suspicion, the inventors tried the nasal drops on additional volunteers who had influenza. These individuals then found that their influenza symptoms were relieved in a relatively short time, two days. The inventors concluded that the Ecbalium evaporate likely contained an anti-viral and additionally might not contain the toxic part of *Ecbalium elaterium*. They thought that the evaporate was present at 40 degrees C., as this was roughly the summer temperature in which the *Ecbalium elaterium* was stored and the discoloring of the covering aluminum occurred. After discarding use of water, methyl alcohol, and ethyl alcohol, the inventors tried Methylene chloride. Methylene chloride is not soluble in water, has mild polarity, and boiling point of 30 to 32 degrees C.

The inventors added the same volume of the solvent, Methylene chloride, and the yield differentiated distillation (using tape water and fresh Ecbalium fruit), then hand shaking for about five minutes in a separating funnel, then leaving the mixture for 30 minutes. This last step gives the solvent a chance for the solvent to be separated form the water due to the different densities. The solvent, which contained the *Ecbalium elaterium* residue, was then transferred to a rotary evaporation machine. The machine evaporated the solvent away at 29 to 30 degrees C., under vacuum. This process yielded about a half milliliter of residue over a period of time of 3 to 4 hours. The residue was a strong smelling brown oily substance.

A HPLC machine analyzed the above final residue. The result was the largest indication of absorption at 8.648 AU (Angstrom) but the substance remains chemically unidentified. The mechanism of action may be similar to that found by others in extract from Aloe Vera. (See U.S. Pat. No. 5,118,673 Carpenter, et al. Jun. 2, 1992 Uses of aloe products).

The residue was gathered into drops and these drops were administered nasally, orally, or topically, in the instance of treatment for herpes zoster. The use of the drops in successfully treating hepatitis, as shown in the inventor's parallel patent application, and in treating influenza, the common cold and herpes zoster, gives a strong indication that the drops are a general anti-viral, even if the particular mode of action is not now known.

Examples of treatment with the *Ecbalium elaterium* residue drops are as follows

EXAMPLE 1

Influenza

Thirty patients, suffering from influenza were given 2 *Ecbalium elaterium* residue drops daily intranasal. The patients included 20 males and 10 females. The age range of the patients ranged from 2.5 years old to 53 years old. All were free from any illness, other than influenza in the acute condition. Twenty-five (25) patients were given the *Ecbalium elaterium* drops and 5 patients received only distilled water drops.

This single blind study showed:

Group A (Patients that Received the *Ecbalium elaterium* Residue Drops)
Number: 30
Gender
Female: 10     Male: 20
Duration of Treatment: 2 hours to 2 days
Symptoms Relieved after Treatment:
High fever and prostration: 27 (90%)
Headache: 24 (80%)
Cough: 18 (60%)
Acute conditions: 30 (100%)

Group B (Patients that Received Only Distilled Water Drops)
Number: 5
Gender
Female: 2

Male: 3
Duration of Treatment: 2 days
Symptoms Relieved after Treatment:
High fever and prostration: 0
Headache: 0
Cough: 0
Acute conditions: 0

EXAMPLE 2

The Common Cold

Fifty patients, suffering from the common cold in acute condition, were given 2 drops 3 times daily intranasal. The patients included 38 males and 12 females. The age range of the patients ranged from 2 years old to 60 years old. All were free from any illness, other than common cold in the acute condition. Another five patients were given the only distilled water drops. This single blind study showed:

Group A (Patients that Received the *Ecbalium elaterium* Residue Drops)
  Number: 50
  Gender
  Female: 12
  Male: 38
  Recovery Period: 1 hour to 2 days
  Symptoms Relieved after Treatment:
  Excess Nasal Discharge: 45 (90%)
  Headache: 40 (80%)
  Acute conditions: 50 (100%)

Group B (Patients that Received Only Distilled Water Drops)
  Number: 5
  Gender
  Female: 2
  Male: 3
  Duration of Treatment: 2 days
  Symptoms Relieved after Treatment:
  Excess Nasal Discharge: 0
  Headache: 0
  Acute conditions: 0

EXAMPLE 4

Chronic Sinusitis

Four patients suffering from chronic sinusitis were given the *Ecbalium elaterium* residue drops in a dose of 2 drops 3 times daily intranasal for a period of 2 months. The patients were one female age 45 and three males ages 31, 33, and 43. Three of them are hepatic patients while the remaining one is non-hepatic.

For three patients, 75% of those in the study, no nasal problems could be seen again, no headache, nasal passages were cleared; with decrease of nasal discharge.

EXAMPLE 5

Herpes Zoster

Diagnosis:
  Case one: a female patient aged 62 years old, was presenting with Herpes zoster in chest region; being in the form of bilateral vesicles along the course of the 6th costal nerve, in addition to a cluster of eruptions in the back of chest region. A cluster of eruptions was detected in scalp region. The group of vesicles was on erythematous base. Vesicles were associated with severe neuralgic pain.

Case two: a 40 years old male patient was suffering from Herpes zoster in left auxiliary region. The description of lesions is as in the previous case.

Treatment:
  The *Ecbalium elaterium* residue was applied on the skin eruptions for both patients twice a day for two days.

Results:
  Both patients' painful eruptions healed completely within 4 days. Follow-up of these patients did not reveal new eruptions or painful areas over a period of 2 months to the date of this application No complications occurred such as post Herpetic neuralgia, secondary infection or skin gangrene.

On insillation of *Ecbalium elaterium* herbal drops, healing occurred within 5 days leaving skin depigmentation in a part of this area Weakly follow-up for 1 month of this patient, the disease did not recur or any complications occurred.

EXAMPLE 6

Herpes Simplex

Diagnosis:
  A male patient 33 years old, was presenting with Herpes fascialis (on the face) on the right side of upper lip. This was represented with groups of vesicles on erythematous base with slight burning sensation.

Treatment
  *Ecbalium elaterium* residue drops were applied to on the patient's lesions Results
  Within a period of 3 days, skin eruptions were treated leaving normal skin. Follow-up Weakly for 5 weeks showed no other attack or recurrence.

We claim:

1. A method for treating symptoms of a viral infection, the viral infection selected from the group consisting of influenza, the common cold and sinusitis, comprising administering to a subject in need thereof a pharmaceutically effective amount of a herbal composition comprising an agent prepared by a method which comprises extracting fruit of *Ecbalium elaterium* with water, allowing the extract to evaporate and collecting a resultant brown evaporate residue, wherein said resultant brown residue is the agent.

2. The method according to claim 1, wherein the viral infection is influenza.

3. The method according to claim 2, wherein the subject is a human.

4. The method according to claim 1, wherein the subject is a mammal.

5. The method according to claim 4, wherein the mammal is a human.

6. The method according to claim 1, wherein the viral infection is the common cold.

7. A method according to claim 6, wherein the subject is a human.

8. The method according to claim 1, wherein the viral infection is sinusitis.

9. The method according to claim 8, wherein the subject is a human.

10. The method according to claim 9, wherein the sinusitis is chronic sinusitis.

* * * * *